United States Patent
Løype

(10) Patent No.: US 11,986,148 B2
(45) Date of Patent: May 21, 2024

(54) ERGONOMIC CONTROL HANDLE FOR INTERVENTIONAL IMAGING PROBE

(71) Applicant: GE Precision Healthcare LLC, Wauwatosa, WI (US)

(72) Inventor: Birger Løype, Horten (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 177 days.

(21) Appl. No.: 17/393,589

(22) Filed: Aug. 4, 2021

(65) Prior Publication Data
US 2023/0040340 A1 Feb. 9, 2023

(51) Int. Cl.
*A61B 1/00* (2006.01)

(52) U.S. Cl.
CPC ...... *A61B 1/00066* (2013.01); *A61B 1/00048* (2013.01); *A61B 1/00013* (2013.01)

(58) Field of Classification Search
CPC ............ A61B 1/00013; A61B 1/00048; A61B 1/00066; A61B 1/0052
See application file for complete search history.

(56) References Cited

U.S. PATENT DOCUMENTS

| | | | | |
|---|---|---|---|---|
| 4,733,337 A | * | 3/1988 | Bieberstein | F21L 2/00 362/198 |
| 5,402,793 A | * | 4/1995 | Gruner | A61B 8/4461 600/463 |
| 2011/0295242 A1 | * | 12/2011 | Spivey | A61B 17/07207 606/1 |
| 2013/0158379 A1 | * | 6/2013 | Selkee | A61B 18/00 604/95.04 |
| 2013/0172813 A1 | * | 7/2013 | Caples | A61B 18/1492 604/95.04 |

* cited by examiner

*Primary Examiner* — Aaron B Fairchild
(74) *Attorney, Agent, or Firm* — Boyle Fredrickson S.C.

(57) ABSTRACT

An invasive interventional device or probe for use in an interventional medical procedure includes a control handle operably connected to an imaging system and an insertion tube. The body having an exterior cross-sectional shape and defining an interior with an interior cross-sectional shape. The body is formed with a pair of opposed side panels, a pair of opposed end panels joining opposite ends of the pair of side panels, a top panel disposed over and joined to the pair of side panels and the pair of end panels and a bottom panel located opposite the top panel and joined to the pair of side panels and the pair of end panels with one or more control elements disposed on the body that control the operation of the interventional device. In addition, the exterior cross-sectional shape of the body conforms to a space defined within a hand in a relaxed grip position.

19 Claims, 9 Drawing Sheets

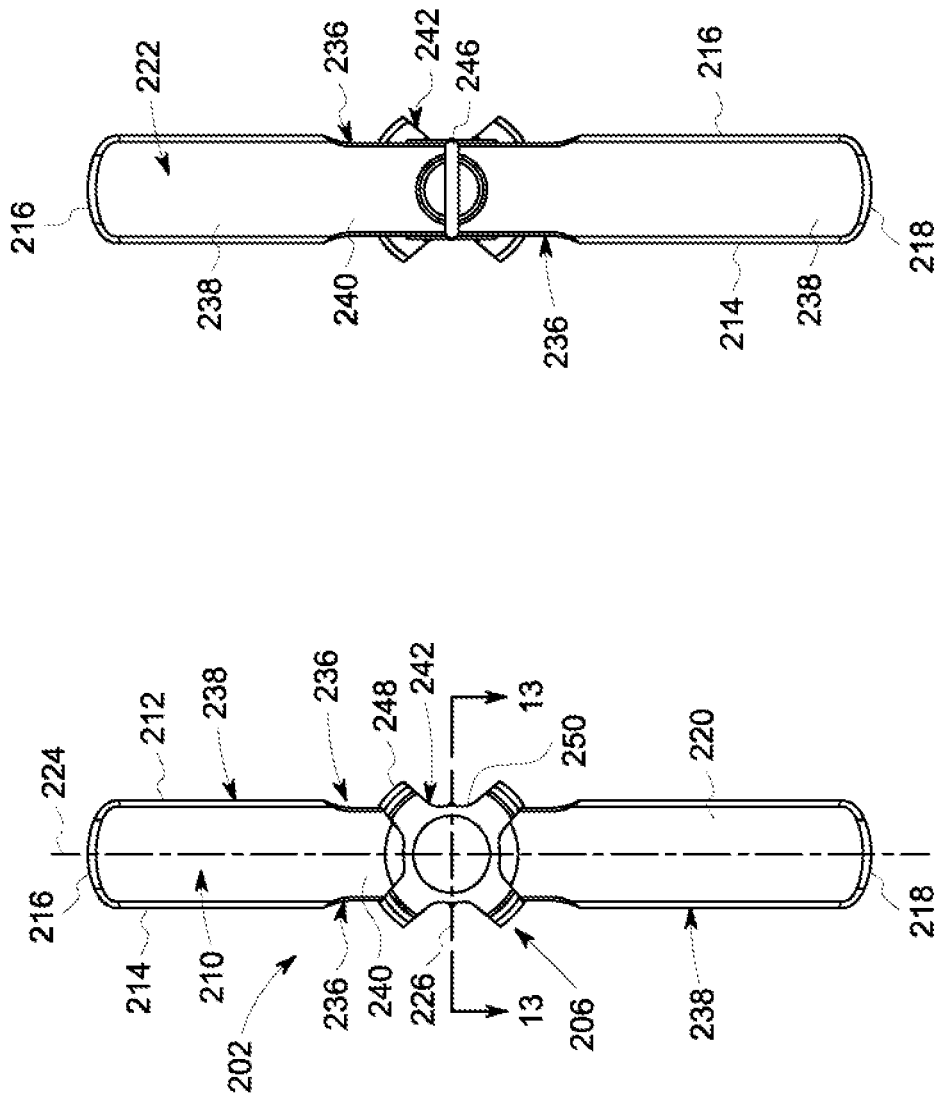

ERGONOMIC CONTROL HANDLE FOR INTERVENTIONAL IMAGING PROBE

BACKGROUND OF THE INVENTION

Embodiments of the present disclosure relate generally to interventional imaging and, more particularly, to structures of control handles used for manipulation of the interventional imaging probes and their method of operation in interventional procedures.

Various medical conditions affect internal organs and structures. Efficient diagnosis and treatment of these conditions typically require a physician to directly observe a patient's internal organs and structures. For example, diagnosis of various heart ailments often requires a cardiologist to directly observe affected areas of a patient's heart. Instead of more intrusive surgical techniques, ultrasound imaging is often utilized to directly observe images of a patient's internal organs and structures.

By way of example, interventional procedures such as transesophageal echocardiography (TEE) and/or intracardiac echocardiography (ICE) may be used to provide high resolution images of intracardiac anatomy. The high-resolution images, in turn, allow for real-time guidance of interventional devices daring structural heart disease (SHD) interventions such as transcatheter aortic valve implantation (TAVI), paravalvular regurgitation repair, and/or mitral valve interventions.

TEE procedures are typically performed in examination, intervention and operating room (open heart surgery) situations where imaging of internal structures of the patient is required. The device utilized in performing TEE typically includes an invasive or interventional device or probe, a processing unit, and a monitor. The probe is connected to the processing unit which in turn is connected to the monitor. In operation, the processing unit sends a triggering signal to the probe. The probe then emits ultrasonic signals via an imaging element within the probe into the patient's heart. The probe then detects echoes of the previously emitted ultrasonic signals. Then, the probe sends the detected signals to the processing unit which converts the signals into images. The images are then displayed on the monitor. The probe typically includes a semi-flexible insertion tube that includes a transducer located near the end of the probe.

Typically, during TEE, the insertion tube is introduced into the mouth of a patient and positioned in the patient's esophagus. The insertion tube is then positioned so that the transducer is in a position to facilitate heart imaging. That is, the insertion tube is positioned so that the heart or other internal structure to be imaged is in the direction of view of the imaging element or transducer disposed within the insertion tube. Typically, the transducer sends ultrasonic signals through the esophageal wall that conic into contact with the heart or other internal structures. The transducer then receives the ultrasonic signals as they bounce back from various points within the internal structures of the patient. The transducer then sends the received signals back through the insertion tube typically via wiring. After the signals travel through the insertion tube and probe, the signals enter the processing unit typically via wires connecting the probe to the processing unit.

Often, in addition to the heart, it may be desirable to image other internal structures within the body of a patient using other interventional imaging procedures and devices, including bronchoscopes or colonoscopes, for example. Imaging other internal structures may require re-positioning or use of a different probe in order to view the internal organs or other internal structures of the patient that are desired. Additionally, viewing the heart and/or other internal structures from various angles and perspectives may require re-positioning of the probe during these procedures.

Although TEE allows for well-defined workflows and good image quality, TEE may not be suitable for all cardiac interventions. Accordingly, in other interventional procedures, ICE may be used to provide high resolution images of cardiac structures, often under conscious sedation of the patient. Furthermore, ICE equipment, which utilizes probes highly similar in construction to those used for TEE, may be interfaced with other interventional imaging systems, thus allowing for supplemental imaging that may provide additional information for device guidance, diagnosis, and/or treatment. For example, a CT, MRI, PET, ultrasound, fluoroscopy, electrophysiology, and/or X-ray imaging system may be used to provide supplemental views of an anatomy of interest in real-time to facilitate ICE-assisted interventional procedures.

In either of these procedures or in any similar invasive or interventional procedure, as previously discussed, the probe or interventional device inserted into the patient includes a control handle with an elongate, flexible insertion tube extending outwardly from the handle. The tube encloses a suitable movement mechanism that is operably connected to a control device on the control handle, such that an operator can control the movement of the mechanism, and the movement of the flexible tube, within the patient. Opposite the control handle, the flexible insertion tube includes an imaging element operable to obtain the ultrasound images of the anatomy of the patient.

In prior art interventional probe control handle configurations, the shape of the handle was adapted from handles utilized in other medical and/or interventional procedures, which had relatively large circular or oval cross-sections to accommodate the internal components required for those procedures, such as circular motors, and to accommodate the components utilized in the construction of the handle itself, such as circular shaft seals disposed between adjacent handle sections.

As the internal components or functional members (i.e., printed circuit board (PCBs) and articulation mechanisms) for control handles for interventional probes used in TEE and related procedures are smaller in size, current control handles 1000, 1002 for TEE interventional probes have a significant amount of dead or unused space 1004 disposed around the internal components and/or functional mechanisms 1006, as shown in FIGS. 1-4. This is due to the reduced size of the functional mechanisms and the rectangular cross-section of those functional mechanisms.

Further, the round (FIGS. 1 and 2) or oval (FIGS. 3 and 4) cross-section of the current control handles does not provide an ergonomic shape to the handle to assist the operator in grasping the control handle in a manner that limits grip fatigue. While a round or oval cross-section for the control handle enables an operator to hold the handle, when utilizing the control structures or elements. i.e., the control wheels and control buttons or knobs, on the handle to control the operation of the probe, the operator needs to be able to readily grasp the handle in a manner that also allows the operator to operate these control structures. With a round or oval cross-section, current handles cannot readily be securely grasped and held by the operator to efficiently operate the control structures during an interventional procedure, as the round or oval cross-section of the handle requires the operator to continuously actively grip the handle to avoid slippage of the handle relative to the hand of the operator. This problem is exacerbated when the control handle becomes slippery, such as when the handle and/or the hands of the user become coated with the gel commonly utilized along with the interventional device in the procedure.

In addition, the large size of current control handles results in the control handle having a significant weight. With an interventional procedure taking as long as a number of hours to complete, this weight can easily fatigue the operator during the extended length of time the operator must continua old the control de during the length of the interventional procedure.

Therefore, it is desirable to develop a structure for a control handle of an invasive/interventional device or probe utilized in an interventional medical procedure that can significantly reduce the unused space within the control handle while additionally reducing grip fatigue of the operator while holding and operating the control handle during the procedure.

BRIEF DESCRIPTION OF THE DISCLOSURE

In one exemplary embodiment of the invention, a control handle for an interventional medical device, includes a body having an exterior cross-sectional shape and defining an interior with an interior cross-sectional shape, the body including a pair of opposed side panels, a pair of opposed end panels joining opposite ends of the pair of side panels, a top panel disposed over and joined to the pair of side panels and the pair of end panels and a bottom panel located opposite the top panel and joined to the pair of side panels and the pair of end panels, and one or more control elements disposed on the body and adapted to control the operation of the interventional device, wherein the exterior cross-sectional shape of the body conforms to a space defined within a hand in a relaxed grip position In another exemplary embodiment of the invention, an interventional medical device includes an insertion tube assembly and a control handle operably connected to the insertion tube and adapted to be connected to an imaging system, wherein the control handle includes a body having an exterior cross-sectional shape and defining an interior with an interior cross-sectional shape, the body having a pair of opposed side panels, a pair of opposed end panels joining opposite ends of the pair of side panels, a top panel disposed over and joined to the pair of side panels and the pair of end panels and a bottom panel located opposite the top panel and joined to the pair of side panels and the pair of end panels, and one or more control elements disposed on the body and adapted to control the operation of the interventional device, wherein the pair of side panels have flat exterior surfaces.

In still another exemplary embodiment of the method of the invention, an imaging system for use in an interventional medical procedure includes an interventional medical device having a control handle with a body having an exterior cross-sectional shape and defining an interior with an interior cross-sectional shape, the body including a pair of opposed side panels with flat exterior surfaces, a pair of opposed end panels joining opposite ends of the pair of side panels, a top panel disposed over and joined to the pair of side panels and the pair of end panels and a bottom panel located opposite the top panel and joined to the pair of side panels and the pair of end panels, one or more control mechanisms disposed within the interior of the body, and one or more control elements disposed on the body and operably connected to the one or more control mechanisms to control the operation of the control mechanisms, and an insertion tube assembly connected to the control handle and including an imaging subsystem for acquiring image data, and a processing unit operably connected to the control handle of the interventional medical device and the imaging subsystem, the processing unit configured to receive and process the image data from the imaging subsystem.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 10 is a top plan view of the control handle of FIG. 6.

FIG. 11 is a bottom plan view of the control handle of FIG. 6.

DETAILED DESCRIPTION

Figure 1:
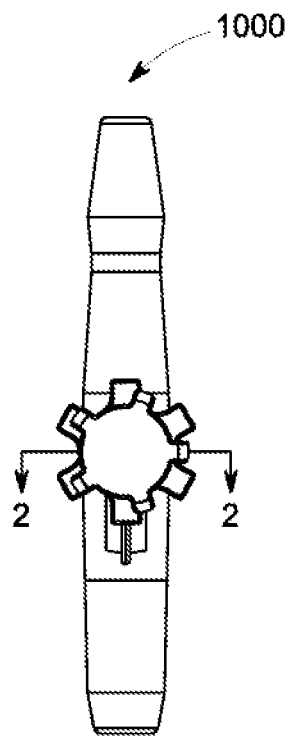
FIG. 1 is a top plan view of a first prior art control handle.
Figure 2:
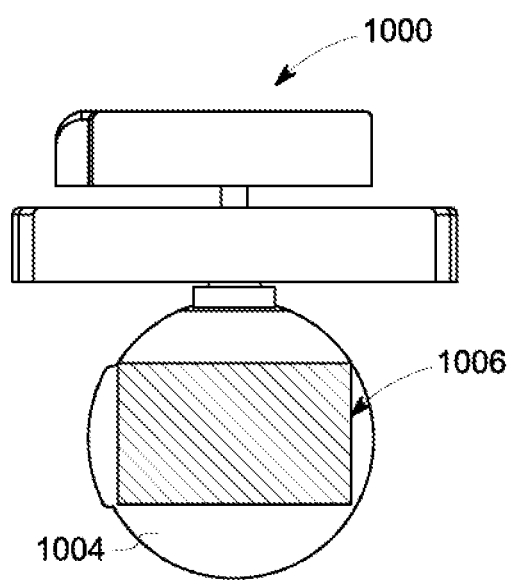
FIG. 2 is a cross-sectional view along line 2-2 of FIG. 1
Figure 3:
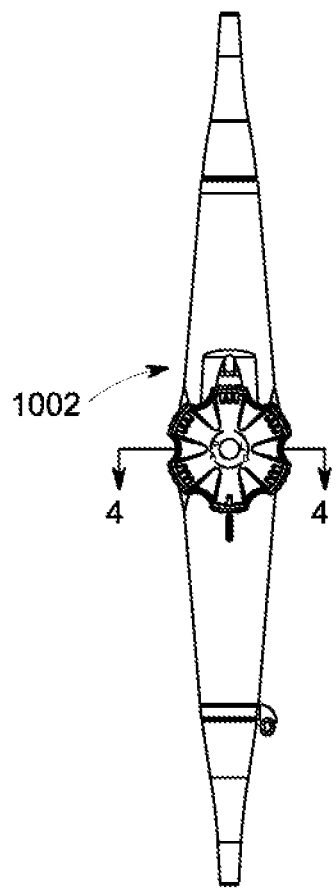
FIG. 3 is a top plan view of a second prior art control handle.
Figure 4:
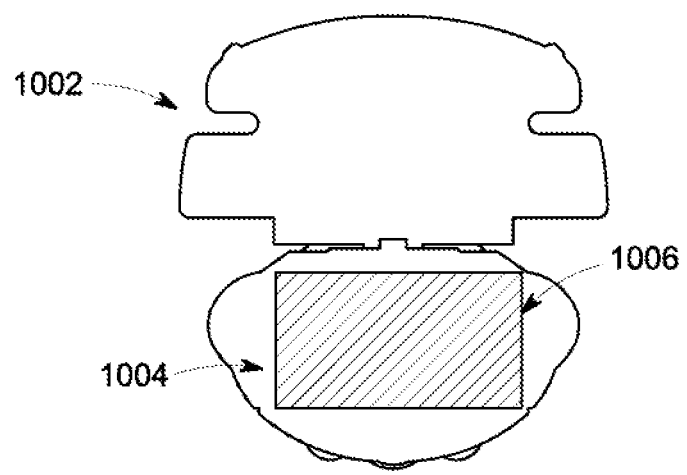
FIG. 4 is a cross-sectional view along line 4-4 of FIG. 3.
Figure 5:
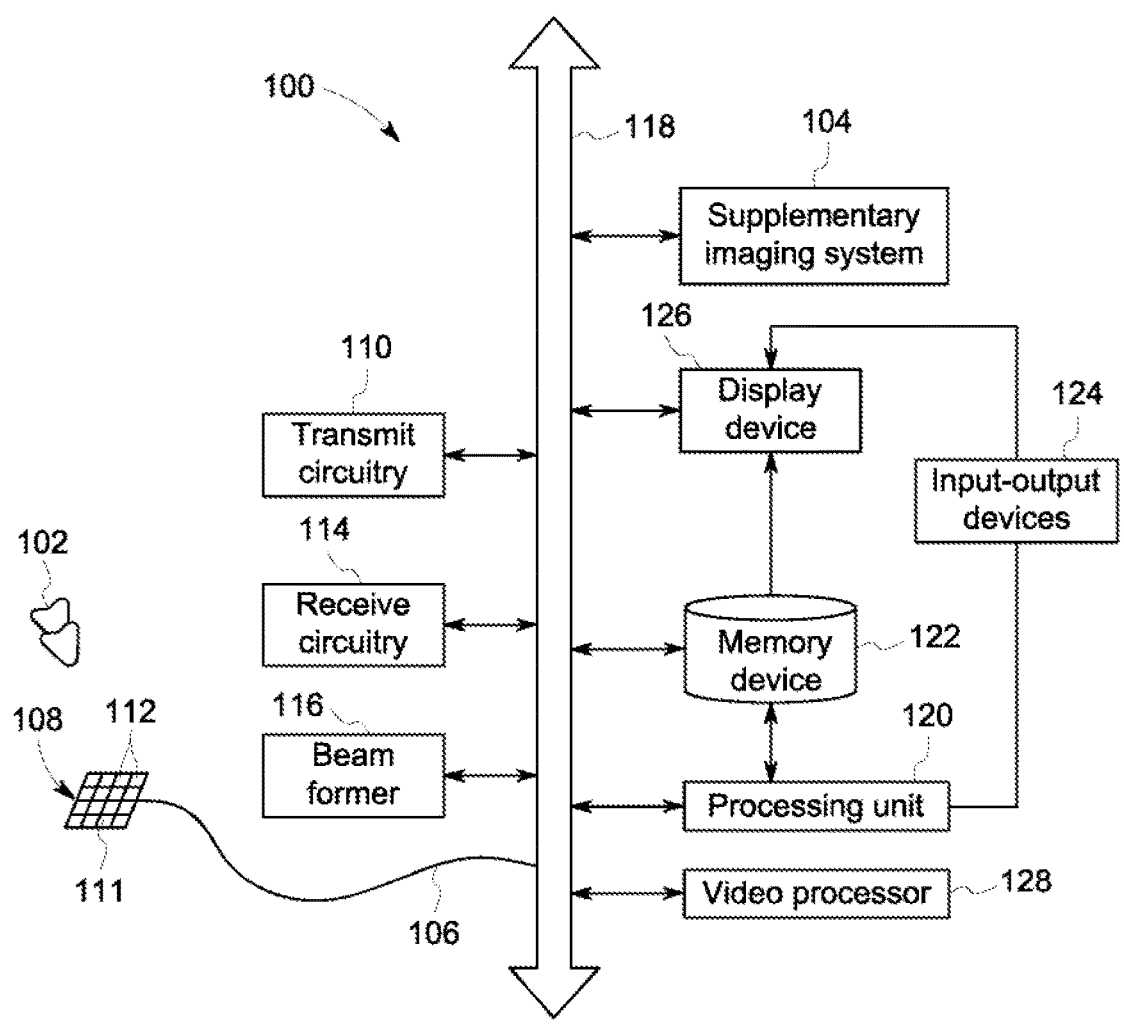
FIG. 5 is a schematic representation of an exemplary imaging system, in accordance with aspects of the present disclosure.

FIG. 5 illustrates an exemplary imaging system 100 for optimal visualization of a target structure 102 for use during interventional procedures. For discussion purposes, the system 100 is described with reference to a TEE system. However, in certain embodiments, the system 100 may be implemented in other interventional imaging systems such as a TTE system, a ICE system, an OCT system, a magnetic resonance imaging (MRI) system, a CT system, a positron emission tomography (PET) system, and/or an X-ray system. Additionally, it may be noted that although the present embodiment is described with reference to imaging a cardiac region corresponding to a patient, certain embodiments of the system 100 may be used with other biological tissues such as lymph vessels, cerebral vessels, and/or in non-biological materials.

In one embodiment, the system 100 employs ultrasound signals to acquire image data corresponding to the target structure 102 in a subject. Moreover, the system 100 may combine the acquired image data corresponding to the target structure 102, for example the cardiac region, with supplementary image data. The supplementary image data, for example, may include previously acquired images and/or real-time intra-operative image data generated by a supplementary imaging system 104 such as a CT, MRI, PET, ultrasound, fluoroscopy, electrophysiology, and/or X-ray system. Specifically, a combination of the acquired image data, and/or supplementary image data may allow for generation of a composite image that provides a greater volume of medical information for use in accurate guidance for an interventional procedure and/or for providing more accurate anatomical measurements.

Accordingly, in one embodiment, the system 100 includes an interventional device or probe 106 such as an ultrasound probe, a laparoscope, a bronchoscope, a colonoscope, needle, a catheter and/or an endoscope. The interventional device 106 is adapted for use in a confined medical or surgical environment such as a body cavity, orifice, or chamber corresponding to a subject, e.g., a patient. The interventional device 106 may further include at least one imaging subsystem 108 disposed at a distal end of the interventional device 106. The imaging subsystem 108 may be configured to generate cross-sectional images of the target structure 102 for evaluating one or more corresponding characteristics. Particularly, in one embodiment, imaging subsystem 10 is configured to acquire a series of three-dimensional (3D) and/or four-dimensional (4D) ultrasound images corresponding to the subject, though the subsystem 108 can also obtain one-dimensional (1D) and two-dimensional (2D) ultrasound images. In certain embodiments, the system 100 may be configured to generate the 3D model relative to time, thereby generating a 4D model or image corresponding to the target structure such as the heart of the patient. The system 100 may use the 3D and/or 4D image data, for example, to visualize a 4D model of the target structure 102 for providing a medical practitioner with real-time guidance tier navigating the probe/interventional device 106 within the patient.

To that end, in certain embodiments, the imaging subsystem 108 can be an ultrasound imaging, system that includes transmit circuitry 110 that may be configured to generate a pulsed waveform to operate or drive an imaging element 111, such as one or more transducer elements 112. The transducer elements 112 are configured to transmit and/or receive ultrasound energy and may comprise any material that is adapted to convert a signal into acoustic energy and/or convert acoustic energy into a signal. For example, the transducer elements 112 may be a piezoelectric material, such as lead zirconate titanate (PZT), or a capacitive micromachined ultrasound transducer (CMUT) according to exemplary embodiments. The interventional device 106 may include more than one transducer element 112, such as two or more transducer elements 112 arranged in an array, or separated from each other on the interventional device 106. The transducer elements 112 produce echoes that return to the transducer elements 112 and are received by receive circuitry 114 for further processing. The receive circuitry 114 may be operatively coupled to a beamformer 116 that may be configured to process the received echoes and output corresponding radio frequency (RF) signals.

Further, the system 100 includes a processing unit 120 communicatively coupled to the acquisition/imaging subsystem 108, to operatively connect the processing unit 120 to the beamformer 116, the interventional device 106, and/or the receive circuitry 114, over a wired or wireless communications network 118. The processing unit 120 may be configured to receive and process the acquired image data, for example, the RF signals according to a plurality of selectable ultrasound imaging modes in near real-time and/or offline mode.

Moreover, one embodiment, the processing unit 120 may be configured to store the acquired volumetric images, the imaging parameters, and/or viewing parameters in a memory device 122. The memory device 122, for example, may include storage devices such as a random access memory, a read only memory, a disc drive, solid-state memory device, and/or a flash memory. Additionally, the processing unit 120 may display the volumetric images and or information derived from the image to a user, such as a cardiologist, for further assessment on a operably connected display 126 for manipulation using one or more connected input-output devices 124 for communicating information and/or receiving commands and inputs from the user, or for processing by a video processor 128 that may be connected and configured to perform one or more functions of the processing unit 120. For example, the video processor 128 may be configured to digitize the received echoes and output a resulting digital video stream on the display device 126.

Figure 6:
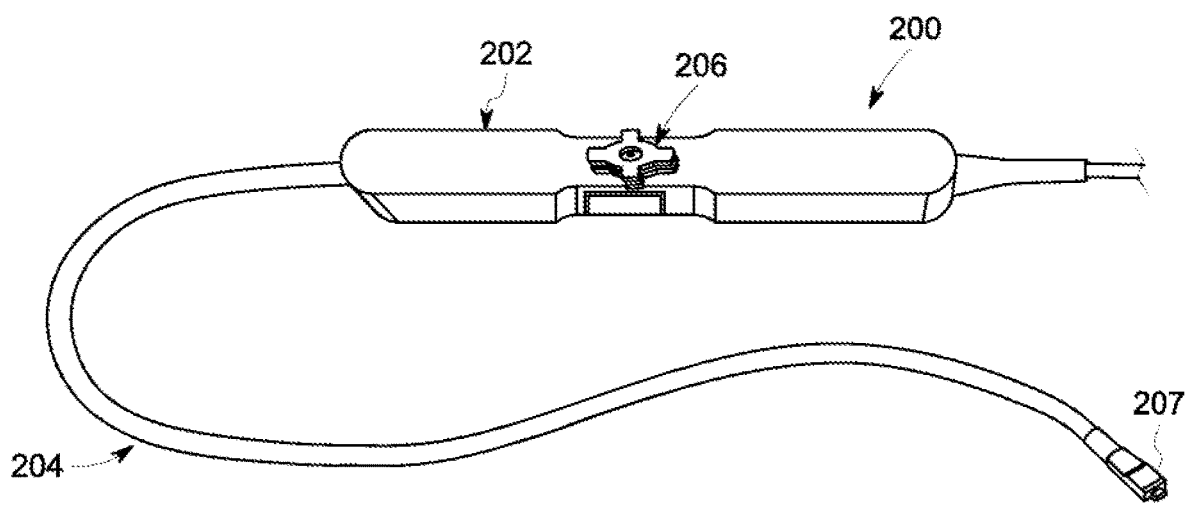
FIG. 6 is an isometric view of an interventional device including a control handle constructed according to a first exemplary embodiment of the disclosure and operable with an ultrasound imaging system.

Referring now to FIG. 6, the interventional device 106 is disclosed in the illustrated exemplary embodiment as being formed as an ultrasound probe/TEE probe 200. The ultrasound probe 200 includes a control handle 202 that is operatively connected to the processing unit, and an insertion tube 204 extending outwardly from the control handle 202 and that includes a tip 207 opposite the handle 202 within which the imaging subsystem 108 is housed. The control handle 202 includes one or more control elements 206 thereon that enable the operator of the ultrasound probe 200 to control the various operations of the internal movement and imaging mechanisms, and associated wiring and/or other connections (not shown) disposed within hollow interior of the insertion tube 204.

Looking now at the illustrated exemplary embodiments of FIGS. 7-12, the control handle 202 includes an elongate body 210 formed with a pair of opposed side panels/sides 212, 214 joined by a pair of opposed end panels'ends 216, 218. The body 210 additionally includes a top panel 220 and a bottom panel 222 extending between the opposed sides 212, 214 and opposed ends 216, 218 to enclose an interior 223 (FIG. 13) of the body 210. The sides 212, 214, the ends 216, 218, the top panel 220 and the bottom panel 222 are each formed of a lightweight and durable material to form the body 210, such as a plastic or a metal.

Figure 12:
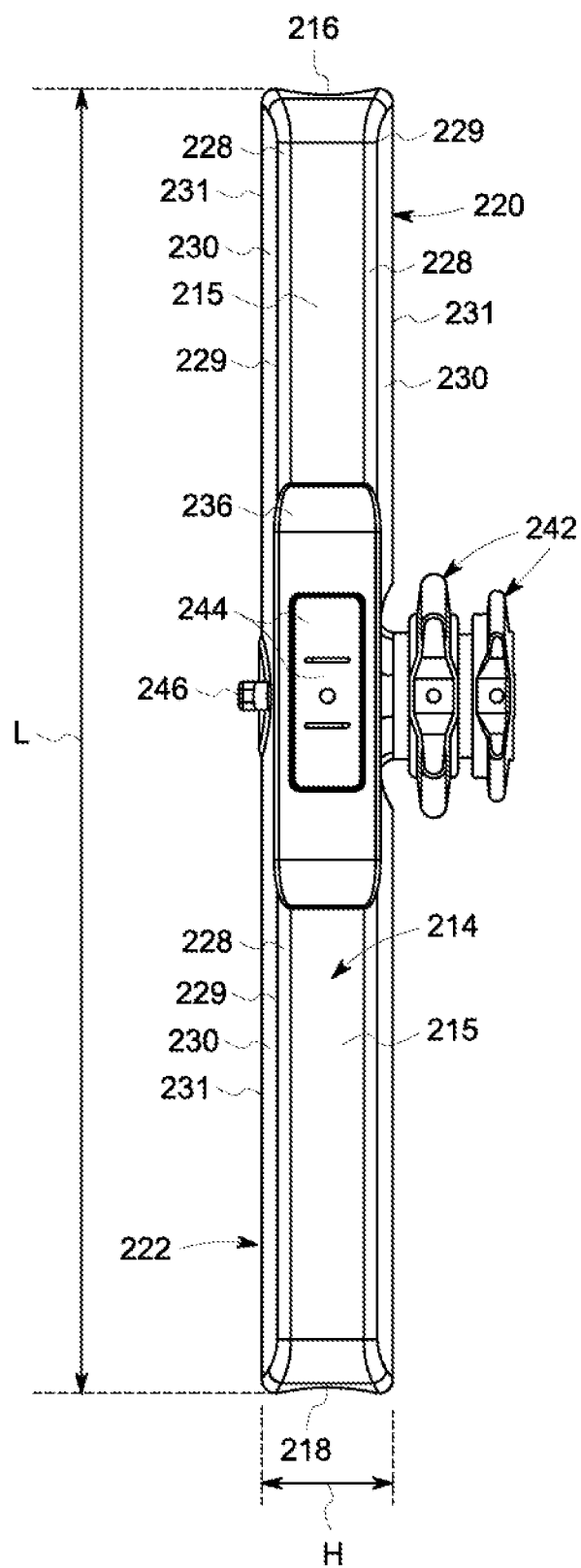
FIG. 12 is a side elevation view of the control handle of FIG. 6.

Referring now to FIGS. 10-12, while the particular configuration of the various components of the body 210 can have any suitable construction to form the body 210, such as a one piece, a two piece, or other multiple piece construction, in the illustrated exemplary embodiment the body 210 is formed to be symmetrical along at least one of a long axis 224 or a short axis 226 of the body 210, or additionally along both the long axis 224 and the short axis 226. By creating this symmetrical shape for the body 210, the ergonomic advantages provided by the body 210 can be utilized when grasping any part of the body 210 during the utilization of the control handle 202 during an interventional procedure.

In the illustrated exemplary embodiment, the top panel 220 and the bottom panel 222 are each formed with a pair of ends 224, 226 that correspond in shape to the opposed ends 216, 218 of the body 210, e.g., having a curved exterior surface 219, and a rounded edge 228 that extends around the perimeter 229 of each of the top panel 220 and the bottom panel 222. The rounded edge 228 provides a smooth surface transition between each of the top panel 220 and the bottom panel 222 and the adjacent opposed sides 212, 214 and ends 216, 218 to enhance the ergonomic configuration and benefits for the body 210.

Each of the top panel 220 and the bottom panel 222 are also formed with an arcuate exterior surface 230. In the exemplary illustrated embodiment, the arcuate surface 230 extends outwardly from the perimeter 229 of each of the top panel 220 and bottom panel 222 to form a crown 231 disposed along the long axis 224 of the body 210. The arcuate surface 230 provides an exterior cross-sectional shape 232 (FIG. 13) for the body 210 along with the opposed sides 212, 214 each including flat exterior surfaces 215 that approximates/conforms in shape to the space 234 (FIGS. 7-8) defined within the hand 400 of a user in a relaxed grip position. In one exemplary embodiment, the curvature of the panels 220, 222 can be defined as a surface continuity between G1-G4 curvatures, as described by https://technologyinarchitecture.com/surface-continuity/, the entirety of which is herein expressly incorporated by reference for all purposes.

Figure 7:
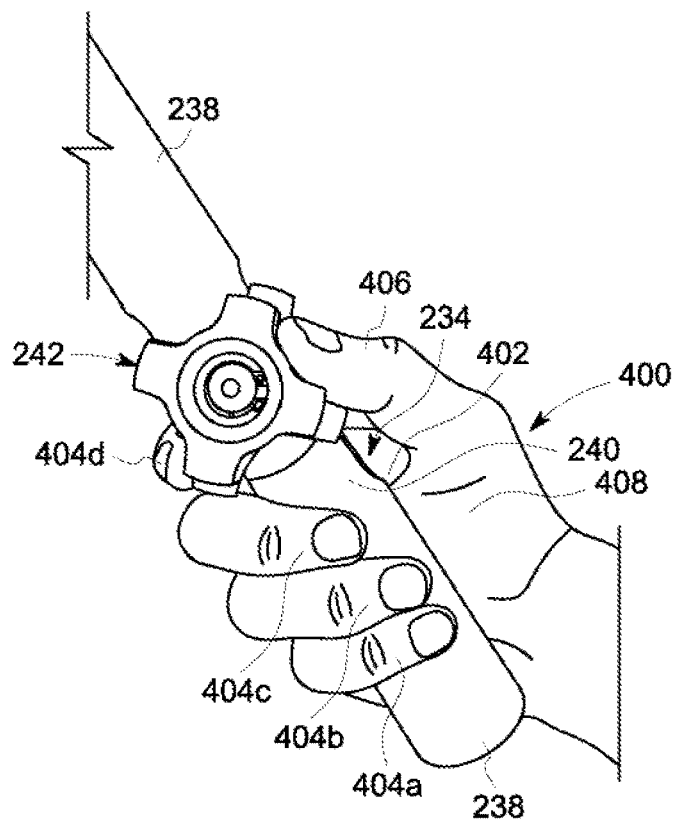
FIG. 7 is a top isometric view of the control handle of FIG. 6 in use.
Figure 8:
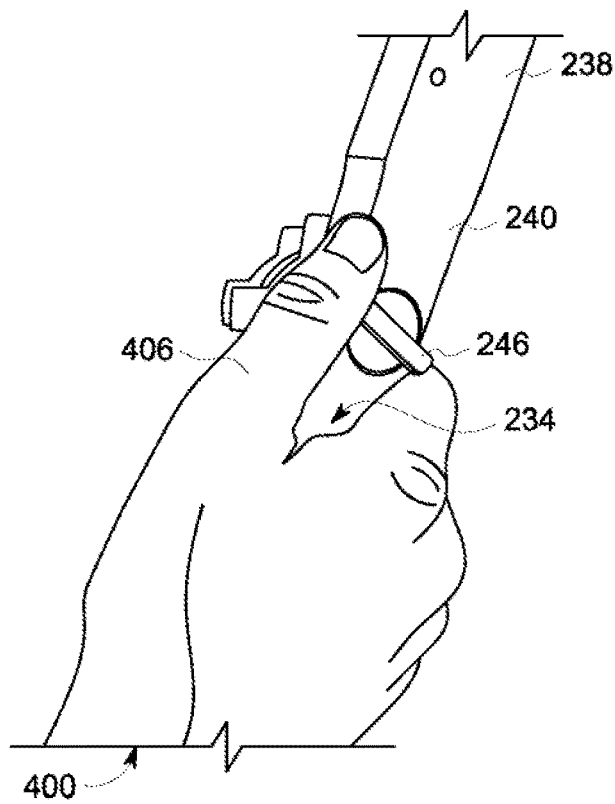
FIG. 8 is a bottom isometric view of the control handle of FIG. 6 in use.
Figure 9:
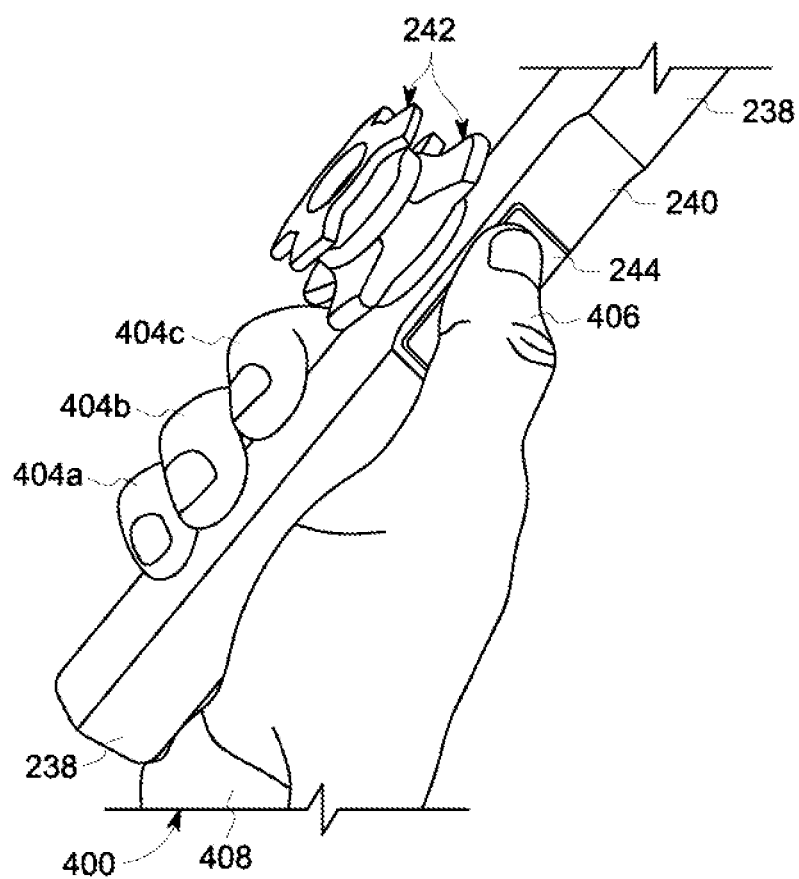
FIG. 9 is a side isometric view of the control handle of FIG. 6 in use.

More specifically, as shown in the illustrated exemplary embodiment of FIGS. 7-9, the arcuate exterior surfaces 230 on the top panel 220 and the bottom panel 222 conform closely to the shape defined by the palm 402 of the hand 400 in a relaxed grip position, allowing the body 210 to be grasped within the hand 400 with minimal grip pressure. The body 210 of the handle 202 is intended to facilitate a relaxed ulnar storage grip to accommodate the 99th percentile of the adult population regardless of gender with both the left hand and right hand. An ulnar storage grip may be defined as a combined storage and internal precision grip where the palm, the little finger and the ring finger is used to hold an object (TEE handle) and the thumb, index finger and long finger is available to perform precision tasks. To assist in holding/gripping the body 210, the flat opposed sides 212, 214 conform closely to the shape of the fingers 404a-404d when disposed in a bent position to grasp the body 210. Further, the height H (FIG. 12) of the opposed sides 212, 214 between the top panel 220 and bottom panel 222 and the width W (FIG. 13) of the top panel 220 and bottom panel 222 enables the fingers 404a-404d to readily and easily wrap around the body 210 from one of the top panel 220 or the bottom panel 222, over the adjacent opposed side 212, or 214, and onto the other of the top panel 220 or the bottom panel 222. In this position, as shown in the illustrated exemplary embodiments of FIG. 7-9, the thumb 406 of the user is positioned against the side 212, 214 opposite the fingers 404a-404d to provide a secure grip around the body 210 of the control handle 202. Further, only relatively light grip pressure is required to be applied from the fingers 404a-404d, and optionally the thumb 406, against the palm 402 to maintain the secure grip on the body 210.

To further facilitate the operation of the control elements 206 on the handle 202, in the illustrated exemplary embodiments of FIGS. 7-13 the flat sides 212, 214, top panel 220 and bottom panel 222 of the body 210 are formed to create a pair of central recesses 236 disposed on the sides of the body 210. The central recesses 236 separate the body 210 of the control handle 202 into a pair of wide end sections 238 and a narrow central section 240. The wider end sections 238 provide the gripping areas on each end of the body 210 for engagement by the hand 400 of the user, while the control elements 206 are located on the narrow central section 240. The control elements 206 located on the narrow central section 240 can be present in any combination of numbers, types, shapes and configurations, but in the illustrated exemplary embodiments include a pair of independently rotatable control wheels 242 disposed coaxially adjacent the top panel 220 for controlling movement of the insertion tube 204, a number of push buttons 244 located on one or both of the sides 212, 214 for controlling operation of the transducer elements 112, and a lock knob 246 disposed on the bottom panel 222 opposite and coaxial with the wheels 242 for controlling the rotation of one or both of the wheels 242. In the illustrated exemplary embodiment, the control wheels 242 are formed with four (4) tabs 248 spaced equidistant from one another on and extending outwardly from a central hub 250. This reduced number of tabs 248 from wheels on prior art control handles that include six (6) tabs significantly increases the ease of cleaning the wheels 242 and the areas, e.g., hubs 250, between the wheels 242 as a result of the increased space between the tabs 248.

As best shown in the exemplary illustrated embodiment of FIGS. 7-9, when the control handle 202 is grasped by a user for operation, the hand 400 of the user is placed against one of the wide sections 238. The palm 402 is disposed against the bottom panel 222 which conforms to the shape of the palm 402 as described previously. The base 408 of the thumb 406 is positioned against one side 212, while the pinkie, ring and middle fingers 404a-404c, respectively, each extend from the palm 402 along the opposite side 214 and over the top panel 220 to provide a secure hold on the wide end 238 when the fingers 404a-404c and thumb 406 are in the relaxed grip position of FIGS. 7-9.

In this position, the index finger 404d and tip 410 of the thumb 406 are located in alignment with the narrow section 240. As such, the index finger 404d and thumb tip 410 are able to engage the control elements 206 located within the narrow section 240, e.g., the control wheels 242, the buttons 244 and the lock knob 246, on each of the sides 212 and/or 214, the top panel 220 and the bottom panel 222, without requiring any shifting of the grip/hand position on the wide section 238. In particular, the smaller width of the body 210 at the narrow section 240 allows the index finger 404d and thumb 406 of the user's hand 400 to easily extend around the control handle 202 to reach and operate the various control dements 206 thereon. With this configuration the exterior of the body 210 of the control handle 202, the user can readily hold the control handle 202 in a secure manner with one hand 400 using only a relaxed grip, such that the user can more easily manipulate the control handle 202 and control elements 206 using the same hand 400 used to grip the handle 202 or the opposite hand, with significantly reduced fatigue over a longer period of time than prior art control handle configurations.

Figure 13:
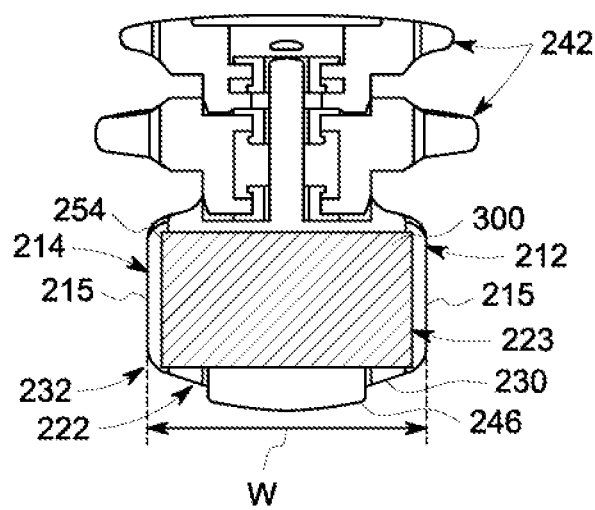
FIG. 13 is a cross-sectional view along line 13-13 of FIG. 10.

Referring now to the illustrated exemplary embodiment of FIG. 13, the interior 223 of the body 210 is formed to have a generally rectangular-shaped interior cross-section 254 along the length L (FIG. 12) of the body 210. With this configuration, the interior 223 closely mirrors the cross-sectional shape of the functional elements and mechanisms 300 that required to be disposed in the interior 223 to provide the desired functionality to the probe 200. This close conformance of the shape of the interior 223 of the control handle body 210 to the shape of the control dements and mechanisms 300 allows the body 210 to hold the required components therein for proper operation of the probe 200, but without the dead space within the interior present in prior art handles. Further, with the configuration of the handle 202 of FIGS. 7-12, the larger mechanisms 300 can be positioned within the interior 223 in one or both of the wide sections 238, e.g., with the mechanisms 300 connected to the imaging system 100 in one wide end 238 and the mechanisms 300 connected to the insertion tube 204 in the opposite wide end 238. Further, the required wiring (not shown) and other connections between the mechanism 300 and the control elements 206 that are disposed on the narrow central section 240, e.g., the wheel shafts 302, 304, can be routed through the narrow section 240 and operably connected to the required mechanisms 300 in the wide ends 238.

Figure 14:
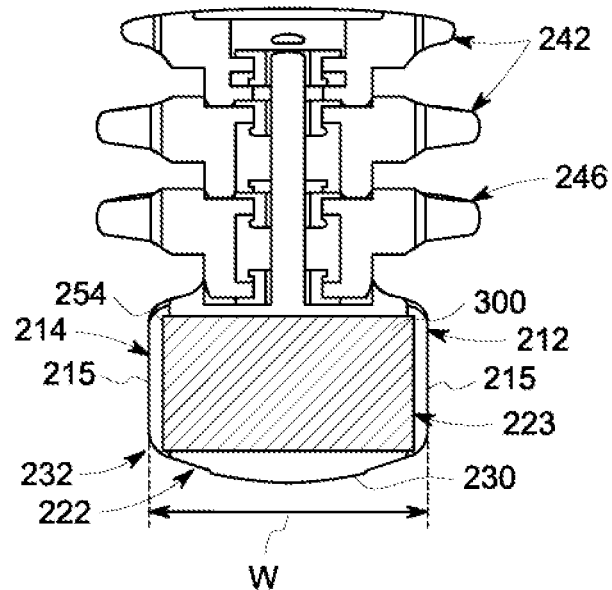
FIG. 14 is a cross-sectional view similar to FIG. 13 of an alternative embodiment of the handle of FIG. 10.

In one alternative embodiment, looking now at the illustrated exemplary embodiment of FIG. 14, the lock knob 246 can additionally be located on the same side of the body 210 as the control wheels 242, as shown in FIG. 14, This arrangement enables the individual to operate each of the control wheels 242 and the lock knob 246 using the index finger 404d and the thumb 406 without having to reposition them on the handle 202.

Figure 15:
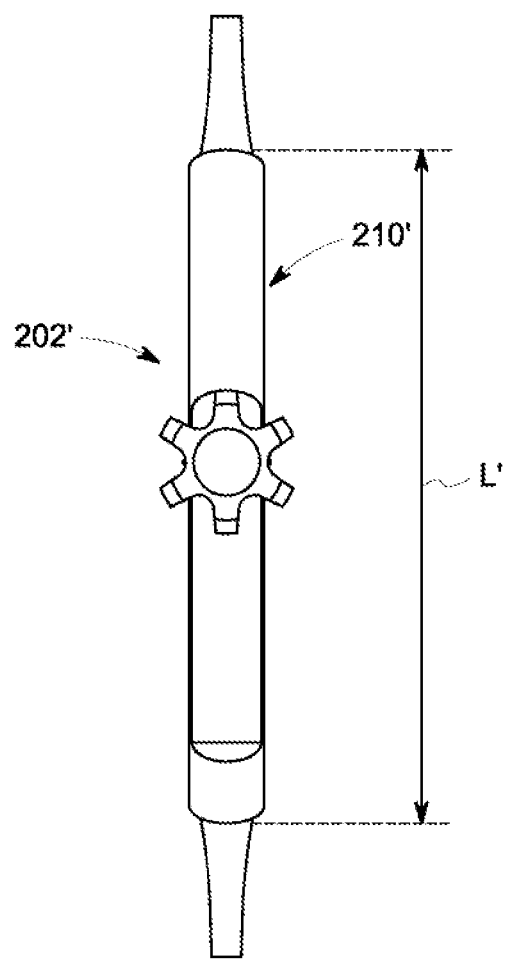
FIG. 15 is a top plan view of a control handle constructed according to a second exemplary embodiment of the disclosure.

Looking now at the additional illustrated exemplary embodiment of FIG. 15, the handle 202' is formed similarly to the handle 202, with the body 210' omitting the recesses 236 and narrow central portion 238. In this embodiment, the body 210' has a generally uniform shape along its entire length L' but with a configuration for the both the interior and exterior cross-sectional shapes of the body 210' similar to that of the body 210 to maintain the ergonomic and space reduction benefits for the handle 202'. Additionally, the body 210' can have optional indents and/or other ergonomic features (not shown) disposed thereon.

In still other alternative embodiments for the control handle 202, the body 210 can be formed with the sides 212, 214 having an exterior surface 215 with a shape other than a flat exterior surface. Additionally, the ends 216, 218 can be formed with an exterior surface 219 other than a curved, surface, such as a flat surface.

In still a further alternative embodiment for the control handle 202, the handle 202 can include one or more various texture enhancing features disposed on one or more of the sides 212, 214 and/or the exterior surface 230 or one or both of the top panel 220 and the bottom handle 222. The texture enhancing features can be formed integrally with the body of the control handle 202, such as indentations, bumps and/or ridges on the various exterior surfaces of the body 210, or can be features applied to the exterior surfaces of the body 210, such as dots or strips of a grip enhancing material, such as a rubber.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A control handle for an interventional medical device, the control handle comprising:
    a body having an exterior cross-sectional shape and providing an interior with an interior cross-sectional shape, the body comprising:
        a pair of opposed side panels wherein the pair of side panels have flat exterior surfaces;
        a pair of opposed end panels joining opposite ends of the pair of side panels;
        a top panel disposed over and joined to the pair of side panels and the pair of end panels; and
        a bottom panel located opposite the top panel and joined to the pair of side panels and the pair of end panels; and
    a plurality of control elements disposed on the body and adapted to control the operation of the interventional device, the plurality of control elements comprising at least two coaxial, independently rotatable wheels.

2. The control handle of claim 1, wherein the pair of end panels have curved exterior surfaces.

3. The control handle of claim 1, wherein the interior cross-sectional shape is a rectangular cross-sectional shape.

4. The control handle of claim 1, wherein the body has at least one axis of symmetry.

5. The control handle of claim 4, wherein the body has at least two axes of symmetry.

6. The control handle of claim 1, wherein the body comprises a central narrow section, and wherein the plurality of control elements are disposed on the narrow section.

7. The control handle of claim 6, wherein the plurality of control elements are rotatably mounted to the central narrow section.

8. The control handle of claim 7, wherein the plurality of control wheels include four outwardly extending tabs thereon.

9. The control handle of claim 6, wherein the body includes at least one wide section disposed adjacent the central narrow section.

10. The control handle of claim 6, wherein the plurality of control elements are contained within a perimeter of the narrow section.

11. The control handle of claim 1, wherein the top panel and the bottom panel each include an outwardly extending exterior surface.

12. The control handle of claim 1, wherein the plurality of control elements further comprises a lock knob disposed on the body opposite the at least two rotatable wheels.

13. The control handle of claim 12, wherein the lock knob is coaxial with the at least two rotatable wheels.

14. An interventional medical device comprising:
    an insertion tube assembly; and
    a control handle operably connected to the insertion tube and adapted to be connected to an imaging system, wherein the control handle comprises:
        a body having an exterior cross-sectional shape and defining an interior with an interior cross-sectional shape, the body comprising:
            a pair of opposed side panels;
            a pair of opposed end panels joining opposite ends of the pair of side panels;
            a top panel disposed over and joined to the pair of side panels and the pair of end panels; and
            a bottom panel located opposite the top panel and joined to the pair of side panels and the pair of end panels; and
        a plurality of control elements disposed on the body and adapted to control the operation of the interventional device, the plurality of control elements comprising at least two coaxial, independently rotatable wheels;
    wherein the pair of side panels have flat exterior surfaces.

15. The interventional medical device of claim 14, wherein the body has at least two axes of symmetry.

16. The interventional medical device of claim 14, wherein the body comprises a narrow section, and wherein the plurality of control elements are disposed on the narrow section.

17. The interventional medical device of claim 14, wherein the interventional medical device is a transesophageal echocardiography probe.

18. An imaging system for use in an interventional medical procedure comprising:
an interventional medical device comprising:
a control handle comprising:
a body having an exterior cross-sectional shape and defining an interior with an interior cross-sectional shape, the body comprising:
a pair of opposed side panels with flat exterior surfaces;
a pair of opposed end panels joining opposite ends of the pair of side panels;
a top panel disposed over and joined to the pair of side panels and the pair of end panels; and
a bottom panel located opposite the top panel and joined to the pair of side panels and the pair of end panels;
one or more control mechanisms disposed within the interior of the body; and
a plurality of control elements disposed on the body and operably connected to the one or more control mechanisms to control the operation of the control mechanisms, the plurality of control elements comprising at least two coaxial, independently rotatable wheels; and
an insertion tube assembly connected to the control handle and including an imaging subsystem for acquiring image data; and
a processing unit operably connected to the control handle of the interventional medical device and the imaging subsystem, the processing unit configured to receive and process the image data from the imaging subsystem.

19. The imaging system of claim 18, wherein the body comprises a narrow section, and wherein the one or more control elements are disposed on the narrow section.

* * * * *